United States Patent [19]

Prince et al.

[11] Patent Number: 4,879,040
[45] Date of Patent: Nov. 7, 1989

[54] ADAPTIVE FILTER CONCENTRATE FLOW CONTROL SYSTEM AND METHOD

[75] Inventors: Paul R. Prince, Fountain Valley; Michael G. Ford, Riverside; Donald W. Schoendorfer, Santa Ana; Ronald L. Clark, Westminster, all of Calif.

[73] Assignee: Baxter International Inc., Deerfield, Ill.

[21] Appl. No.: 291,413

[22] Filed: Dec. 22, 1988

Related U.S. Application Data

[63] Continuation of Ser. No. 166,833, Mar. 4, 1988, abandoned, which is a continuation of Ser. No. 671,576, Nov. 15, 1984, abandoned.

[51] Int. Cl.⁴ ............................................. B01C 13/00
[52] U.S. Cl. .................................... 210/637; 210/651; 210/90
[58] Field of Search ...................... 210/651, 433.2, 90, 210/85, 929, 637, 87; 604/4, 5, 6

[56] References Cited

U.S. PATENT DOCUMENTS 4,370,983 2/1983 Lichtenstein ................... 210/929 X
4,381,999 5/1983 Boucher et al. ..................... 210/637
4,444,596 4/1984 Gortz et al. ....................... 210/90 X
4,486,303 12/1984 Brous ............................... 210/929 X
4,493,693 1/1985 Bilstad et al. .................... 128/630 X

OTHER PUBLICATIONS

International Publication No. WO 85/02783, Jul. 4, 1985 for "Filtration Method and Apparatus" of Josif Shmidt, PCT/US84/02094.
Dorson, Jr., et al., Int. Pub. No. WO82/03567, published 10-28-82, 50 pages.

Primary Examiner—Frank Spear
Attorney, Agent, or Firm—Paul C. Flattery; Gregory Roth; Bradford R. L. Price

[57] ABSTRACT

An adaptive filter concentrate flow control system and method includes a filter system, a pumping system driving feed fluid, concentrate and filtrate flowing through the filter system and a flow control system controlling the pumping system to maintain optimum filtrate flow rates along a control curve in a transmembrane pressure—feed fluid rate—filtrate flow rate three dimensional space. Actual sensed operating point data is used to locate the control curve so as to assure an optimized filtrate flow rate at which reversible blocking of the membrane has begun to occur without irreversible plugging. The system is advantageously employed to control and maximize the flow of plasma in a plasmapheresis system.

31 Claims, 4 Drawing Sheets

ADAPTIVE FILTER CONCENTRATE FLOW CONTROL SYSTEM AND METHOD

This application is a continuation, of application Ser. No. 166,833, filed Mar. 4, 1988, abandoned, which is a continuation of application Ser. No. 671,576, filed Nov. 15, 1984, now abandoned.

BACKGROUND OF THE INVENTION

1. Field of the Invention

This invention relates to the optimization of concentrate flow in a filter system and more particularly to a system using actual sensed operating curve data to optimize plasma flow in a plasmapheresis system.

2. Discussion of the Prior Art

Conventional filtering systems involve a tripartite fluid flow relative to a porous membrane. Feed fluid which is to be filtered is presented to a first side of the membrane and flows across the first side of the membrane along a longitudinal axis of the filter system. Filtrate fluid passes through the membrane and is withdrawn from the second side of the membrane, opposite the first side. Components of the feed fluid which pass along the membrane without passing there-through are drawn off as a retentate or concentrate fluid.

In a typical filtering application such as a plasmapheresis system wherein plasma is separated from whole blood to form a packed cell concentrate, it is desirable to maximize the percentage or absolute flow rate of the filtrate. For moderate filtrate flow rates and fixed membrane area, the filtrate flow rate is approximately proportional to transmembrane pressure (TMP).

However, as the filtrate flow rate increases a reversible blocking effect causes transmembrane pressure to increase more rapidly relative to filtrate flow. The blocking effect is reversible in the sense that if the filtrate flow is decreased after blocking has occurred there is no plugging of the filter pores and the original substantially linear TMP-filtrate flow relationship is reestablished.

However, if the filtrate flow (and TMP) become sufficiently high, red cells, platelets or other particulate matter lodge permanently in the membrane pores and begin to irreversibly plug the filter. The plugging decreases the effective area of the membrane and if continued over a period of time will cause the filtrate flow rate to decrease while the TMP remains constant or even increases, or cause an increase in TMP if the filtrate flow rate is maintained. If the filtrate flow rate is decreased the filter membrane remains partially plugged and the effective area of the membrane is permanently decreased wherein the original TMP-filtrate flow relationship is changed undesirably.

One filter flow control system is partially described in Lysaght, M. J.; Schmidt, B.; Samtleen, W.; and Gurland, H. J. "Transport Considerations in Flat Sheet Microporous Membrane Plasmapheresis," *Plasma Therapy Transfusion Technology*, Vol. 4, No. 4 (1983) pp. 373–85. The described system uses a pumping system with pumps driving the feed fluid (blood) and filtrate (plasma). The control system senses pump flow rates in the feed fluid and filtrate paths and senses pressure in all three filter fluid paths. A clamp also controls the flow of feed fluid over the membrane surface. The sensed information is used by an undisclosed control algorithm to control the filtrate flow and clamp to keep TMP constant and to maintain a desired inlet to outlet pressure differential.

Some systems use a capillary separator in place of a flat membrane device. The capillary separator uses hollow fibers with thin, porous walls. The walls of the fibers are essentially porous membranes and function in a manner similar to a flat membrane. A system using a capillary separator is described in Buchholz, D. H.; Porten, J.; Anderson, M.; Helphigstine, C.; Lin, A.; Smith, J.; Path, M.; McCullough, J.; and Snyder, E.; "Plasma Separation Using the Fenwal COS-10 Capillary Plasma Separator," *Plasmapheresis*, edited by Y. Nose, P. S. Malcesky, J. W. Smith and R. S. Krakauer, Raven Press, New York (1983).

SUMMARY OF THE INVENTION

An adaptive filter fluid flow control system in accordance with the invention includes a filter system having a porous membrane filter, a flow regulating system having pumps coupled to drive feed fluid, concentrate and filtrate through the filter system, a pressure sensor coupled to detect and indicate transmembrane pressure and a filter fluid control system coupled to control the pumping system to optimize filtrate flow rates in response to transmembrane pressure (TMP).

The filter fluid control system detects data for at least one actual system TMP-filtrate flow rate operating point in a flow rate versus transmembrane pressure coordinate system, extrapolates the actual operating point data to form a prediction curve and translates the prediction curve to derive a control curve. The control curve may be optimally rotated relative to the prediction curve to obtain specialized control characteristics.

The filter system is operated at a point where actual system operating characteristics represented by a fluid characteristics curve intersect the control curve. The value by which the control curve is translated relative to the prediction curve is selected to place the operating point at an optimum filtration flow rate at which reversible blocking of the filter device has begun to occur. At this point further increases in filtrate flow would soon damage the filter while a lesser flow would result in the harvesting of less filtrate.

The filter system has particular advantage when used in a plasmapheresis system wherein the feed fluid is whole blood, the concentrate is packed cells and the filtrate is plasma. In a plasmapheresis system the blood flow rate is controlled to match requirements of the donor subject and the plasma flow rate is controlled relative to the blood flow rate. Because the sum of the concentrate and filtrate flow rates must match the feed flow rate, plasma flow rate can be controlled by actively controlling the blood and packed cell flow rates by controlling the speed of peristaltic pumps which pump these fluids.

BRIEF DESCRIPTION OF THE DRAWINGS

A better understanding of the invention may be had from a consideration of the following Detailed Description taken in conjunction with the accompanying drawings in which.

DETAILED DESCRIPTION

Figure 1:
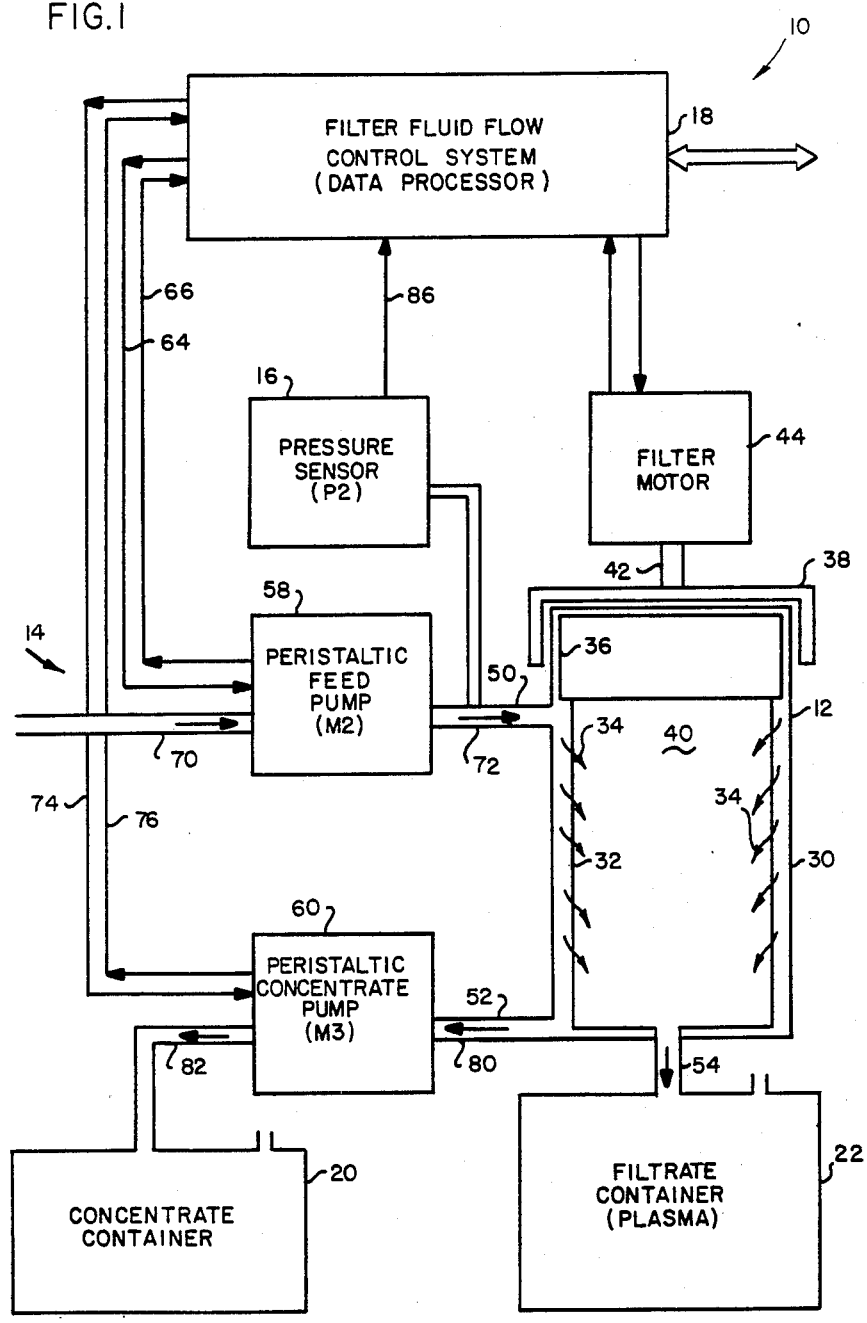
FIG. 1 is a schematic and block diagram representation of an adaptive filter fluid flow control system in accordance with the invention.

Referring now to FIG. 1, there is shown an adaptive filter fluid flow control system 10 in accordance with the invention including a filter system 12, a pumping system 14, a P2 pressure sensor 16, a filter fluid flow control system 18, a concentrate container 20 and a filtrate container 22. While the filter system 10 may be utilized for other appropriate filtering applications, it is particularly useful for filtering plasma from whole blood in a plasmapheresis system. While the disclosure of this patent has been limited in scope to the subject adaptive filter fluid flow control system 10, a more complete disclosure of a plasmapheresis system in which such a filter system 10 might be utilized is found in a co-pending, commonly assigned patent application Ser. No. 06/626,034 filed June 29, 1984 by Paul Prince et al for "Blood Extraction and Reinfusion Flow Control System and Method", now abandoned and superseded by U.S. Pat. No. 4,657,529.

The filter system 12 may alternatively be a stationary flat membrane or capillary separator type of system but is preferably of the vortex enhanced shear flow separator type having a generally cylindrical housing 30 enclosing a cylindrically shaped rotating filter membrane 32 having pores through which a filtrate such as blood plasma may flow as indicated by arrows 34.

Two magnetic pole pieces 36, 38 provide a magnetic coupling through the hermetically sealed filter housing 30 to cause a rotator 40 supporting the filter membrane 32 and magnetic coupling 36 to rotate in response to a filter motor 44 and shaft 42. Filter motor 44 is conventionally driven at a controlled velocity in response to commands from the filter fluid flow control system 18. Filter motor 44 includes position feedback sensing devices in the form of Hall effect devices which return to filter fluid flow control system 18 twelve uniformly distributed pulses for each rotation of filter motor 44.

The present invention is not concerned with the specific configuration of the filter system 12. The filter system 12 has thus been represented in a somewhat schematic and idealized form. However, a more complete description of a preferred configuration for the filter system 12 can be found in a commonly assigned patent application Ser. No. 591,925 filed Mar. 21, 1984 for "Method and Apparatus for Separation of Matter from Suspension", by Donald W. Schoendorfer.

In operation, the filter system 12 receives an anticoagulant protected whole blood feed fluid at an inlet 50. The feed fluid surrounds the cylindrical, rotating membrane 32 and flows longitudinally downward toward a concentrate or retentate outlet 52 through which is discharged the concentrate or retentate which is packed cells for the presently disclosed application of use in a plasmapheresis system. As the feed fluid flows longitudinally downward from the inlet 50 to the outlet 52 a filtrate component thereof, which is plasma in the present instance, passes through pores in the filter membrane 32 as indicated by arrows 34 to exit the filter system 12 through a filtrate outlet 54 which is coupled to the filtrate container 22. The filtrate container 22 is schematically illustrated as being vented to the atmosphere. However, in the preferred embodiment the container 22 is actually a flexible wall bottle or container which maintains the filtrate fluid at atmospheric pressure while isolating the fluid from atmospheric contamination.

The pumping system 14 includes a peristaltic feed pump 58 and a peristaltic concentrate pump 60. The peristaltic feed pump 58 includes a drive motor designated M2 which is coupled in a conventional manner to receive velocity commands from filter fluid flow control system 18 over a control path 64. Like the filter motor 44 the motor M2 driving peristaltic feed pump 58 includes conventional Hall effect position sensor devices which provide to filter fluid flow control system 18 over a feedback path 66 rotational position indicating pulses with 12 pulses distributed over each cycle of rotation of the motor M2. Peristaltic feed pump 58 receives feed fluid through a conduit 70 from a suitable feed fluid source such as a donor subject in the particularly disclosed application and pumps the received feed fluid with a controlled flow velocity to the inlet 50 of filter system 12 through a conduit 72.

The peristaltic concentrate pump 60 is coupled in a conventional manner to receive velocity control signals over a control path 74 from filter fluid flow control system 18. Peristaltic concentrate pump 60 includes a drive motor M3 which receives the velocity control commands and has Hall effect position feedback sensing devices. The Hall effect devices provide to filter fluid control system 18 position feedback signals in the form of 12 pulses uniformly distributed over each rotation of the motor M3. The feedback pulses are communicated to the filter fluid flow control system 18 over a feedback path 76.

Peristaltic concentrate pump 60 receives retentate fluid from outlet 52 over a conduit 80 and pumps the retentate fluid at a controlled flow rate over a conduit 82 to the concentrate container 20. As with the filtrate container 22, the concentrate container 20 is shown having a vent to atmospheric pressure. However, it should be kept in mind that in the present application the concentrate within concentrate container 20 must be protected from atmospheric contamination as by using a filtration type of vent.

It can readily be seen that once the filter system 12 is primed with fluid, the flow of feed fluid through inlet 50 must equal the flow of concentrate fluid through outlet 52 plus the flow of filtrate fluid through outlet 54. Consequently, by controlling the flow of concentrate fluid through peristaltic concentrate pump 60 relative to the flow of feed fluid through peristaltic feed pump 58, the flow of filtrate fluid through outlet 54 is inherently controlled even though no pump is disposed along the filtrate fluid path to directly control the flow of filtrate fluid. It is thus apparent that references to control of the filtrate fluid made in this disclosure can include indirect control over filtrate fluid flow by controlling the feed fluid flow and concentrate fluid flow as well as direct control over filtrate fluid flow.

It is further noted that in general any relative control of the fluid rates through feed pump 58 and concentrate pump 60 can be utilized to control the filtrate fluid flow rate, their difference equalling the filtrate flow rate for incompressible fluids. However, for the present application of a plasmapheresis system, it has been found desirable to control the feed pump 58 independently of the filter system 12 to optimize the extraction of feed fluid from a subject donor serving as the source of feed fluid. The concentrate pump 60 is then controlled relative to the flow rate through the feed pump 58 to produce a system controlled filtrate flow rate through outlet 54. Alternatively, pump 60 could be positioned to control filtrate fluid flow through outlet 54 directly as suggested by dashed line 56. The remaining discussion assumes that pump 60 is positioned along the concentrate, fluid flow path between conduits 80 and 82.

P2 pressure sensor 16 is coupled to sense pressure along the conduit 72 between the peristaltic feed pump 58 and the inlet 50 of filter system 12. Pressure sensor 16 responds to the sensed pressure by generating indications thereof which are communicated over a pressure feedback path 86 to the control system 18. Because pressure sensor 16 is coupled to a path which is in direct flow relationship with an inlet side of the membrane 32 and because the filtrate which is in direct flow relationship with an outlet side of the membrane 32 is maintained at a constant, atmospheric pressure, the pressure sensed by sensor 16 is indicative of transmembrane pressure across the membrane 32, subject to corrections for pressure loss in the conduit 72 between the sensor point and the inlet 50, subject to pressure head that is dependent upon the particular relative elevations of the conduit 72 and the filtrate container 22, subject to centrifugally induced pressures resulting from rotation of the rotor 40, and subject to hydrodynamic pressure loss through the filter device 30.

The structure of the filter fluid flow control system 18 is not disclosed in detail. However, it may be implemented as a conventional microprocessor based control system having conventional analog to digital converters and digital to analog converters coupling the microprocessor to the motors and feedback devices of the adaptive filter system 10. Concentrate container 20 temporarily stores concentrate until full, wherein the plasmapheresis system pauses in the operation of filter 30 in order to return the concentrate to the fluid feed source. A combination of one filtration episode and one concentrate return comprises a filtration cycle.

Figure 2:
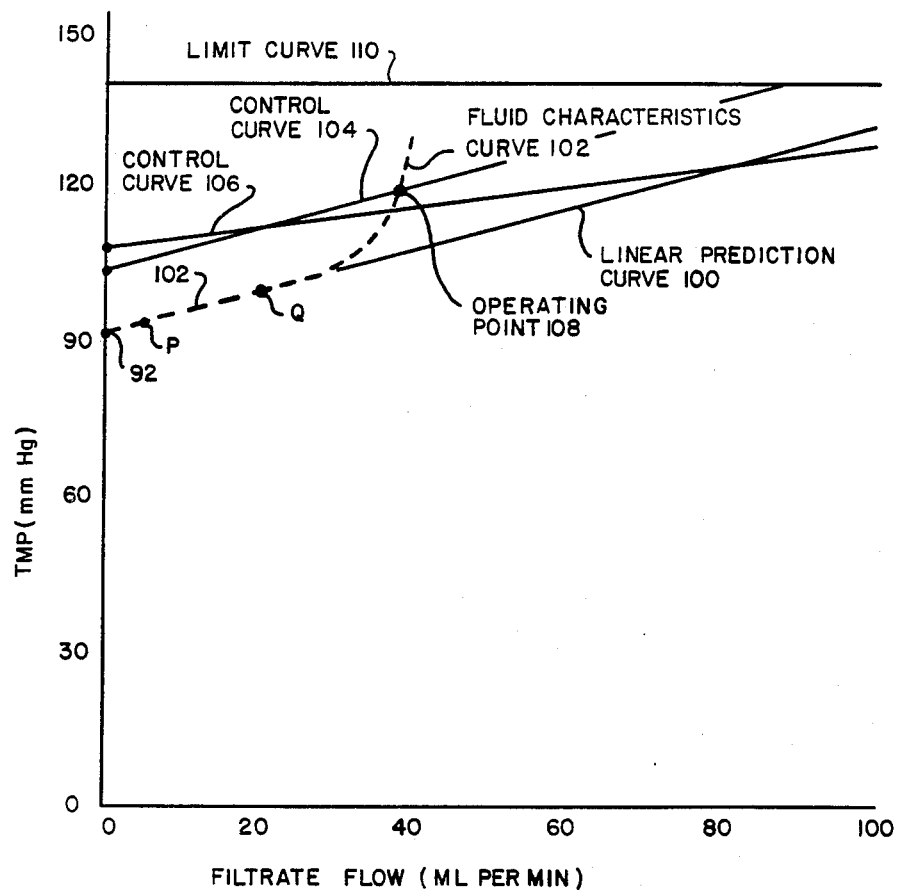
FIG. 2 is a graphical illustration of curves that are useful in understanding the operation of the filter system shown in FIG. 1.

Curves illustrating the method of controlling filtrate flow through a filter system in accordance with the present invention are shown in FIG. 2 to which reference is now made. In the present example each filtration operation or session begins with an initializing interval during which the feed pump 58 is operated at a constant and relatively low feed fluid flow rate of 50 milliliters per minute. This flow rate is selected to be well within the supply rate capacity for the feed fluid. During this initializing interval the filter system 12 is primed with fluid and once stable operation is obtained, initializing measurements are taken. These measurements include the sensing and storing of pressure P2 at one or more relatively low filtrate flow rates. For example, pressure data may be acquired at a flow rate of 5 milliliters per minute as indicated at a point P and at 20 milliliters per minute as indicated at a point Q. Typical operating characteristics would result in a sensed pressure of 94 mm Hg above atmospheric at point P and a pressure of 100 mm Hg above atmospheric at point Q.

The sensed initializing points are then fitted with a prediction curve which in the case of two sensed points might be a straight line forming a linear prediction curve 100. The linear prediction curve 100 will typically have a slope of 8 mm Hg per 20 ml per minute concentrate flow rate and intersect the 0 flow rate axis at 92 mm Hg.

This 92 mm Hg intersection point 92 results from flow rate independent constant pressure offsets occurring at the pressure sensing point near the inlet 50 of filter system 12. While this pressure offset will vary significantly with the particular implementation and use of the filter system 12, when used in a plasmapheresis system, the offset might typically be comprised of 95 mm Hg from centrifugal force induced pressure, −35 mm Hg from the pressure head resulting from elevational differences between the pressure sensor and the filtrate container 22, and 32 mm Hg from convective turbulence forces within the filter system 12. The exact transmembrane pressure is thus the pressure sensed at P2 less these fixed offsets less some additional minor corrections for flow related pressure drops such as drops within conduit 72. However, because these flow rate related pressure changes tend to vary linearly with flow rate as sensed at pressure sensor P2 they will vary linearly at the pressure sensor P2 and can be automatically included in the linear prediction curve 100. The slope of the linear prediction curve 100 thus can be considered to represent changes in actual TMP, although a small percentage of those changes are actually induced by other sources.

At lower plasma flow rates, the actual sensed fluid pressure will follow the linear prediction curve 100. However, as the filtrate flow rate increases (for a constant feed flow rate), the filter membrane or other filter device will begin to experience reversible blocking and actual sensed pressure increases more rapidly than the linear prediction curve 100 as represented by a fluid characteristic curve 102.

Translation of the linear prediction curve 100 upward by an experimentally determined pressure offset of 12 mm Hg results in control curve 104 which intersects the fluid characteristic curve 102 at an operating point 108.

At the operating point 108, filtrate flow is maximized or optimized at a point above the linear prediction curve 100 where reversible blocking has begun to occur but irreversible plugging of the membrane pores is not taking place. If the pressure offset translation magnitude between the linear prediction curve 100 and control curve 104 is made too great, the operating point 108 will occur at a point having too high a TMP and irreversible plugging of the filter membrane 32 will begin to occur. As this plugging proceeds over time the effective membrane area will decrease from the initial area of 40 square centimeters and the slope of the fluid characteristics curve 102 will increase. That is, curve 102 will tend to be translated upward and rotated counter clockwise as the effective filter area is reduced. Hence, the operating point 108 will begin to move toward lower plasma flow rates and down the control curve 104 toward the 0 flow rate axis. However, so long as the offset is chosen to enable the control curve 104 to intersect the fluid characteristic curve 102 at an operating point 108 below the pressure and filtrate flow rate at which irreversible plugging begins to occur, stable operation of the filter system 12 may be obtained at a relatively high filtrate flow rate, maximized by the measurement of the pressure-flow characteristics of the instant filter device and the instant feed fluid characteristics.

Since the control curve 104 is mathematically determined in response to the actual sensed operating point Q, or points P and Q, the slope of the control curve can be varied relative to the linear prediction curve 100 to improve operating conditions which may depend upon the particular application and filtering configuration of the filter system 12. For example, rotation of the control curve about the 20 milliliter per minute flow rate intercept point from a nominal slope of 8 mm Hg, per 20 milliliter per minute flow rate to 4 mm Hg per 20 milliliter per minute flow rate results in a control curve 106. Control curve 106 produces an operating point intercept with fluid characteristics curve 102 slightly below the operating point 108 but its reduced slope also produces a greater differential with respect to the fluid characteristics curve 102 at lower filtrate flow rates. The greater differential can be utilized to cause an error driven flow control system controlling the filtrate flow rate to more rapidly increase the filtrate flow rate toward the eventual relatively high operating point. The lower slope control curve 106 also tends to more severely limit the TMP at the operating point as filtrate flow rate increases. Greater protection against irreversible plugging is thus provided for the filter membrane at higher filtrate flow rates. It will be noted of course that less protection is accordingly afforded at lower filtrate flow rates. It will be appreciated that depending upon the particular fluid characteristics and filter system characteristics, other adaptive control curve shapes might be utilized to optimize operation of the adaptive control system 10.

A limit curve 110 imposes an upper limit of 140 mm Hg on the allowable operating point transmembrane pressure as sensed at P2 pressure sensor 16. Should the detected intersection of the fluid characteristic curve 102 with the control curve 104 indicate an operating point 108 with a TMP greater than 140, the lesser value of 140 is imposed as an operating point. The limit point of 140 mm Hg is selected to be above the anticipated operating point so as to avoid interference with expected normal system operation, yet sufficiently low to protect the filter membrane against rapid plugging should an error condition or unexpected operating condition occur, such as a significant error in the measurement of point P or Q, or unusual variation in the viscosity characteristics of the feed fluid.

Figure 3:
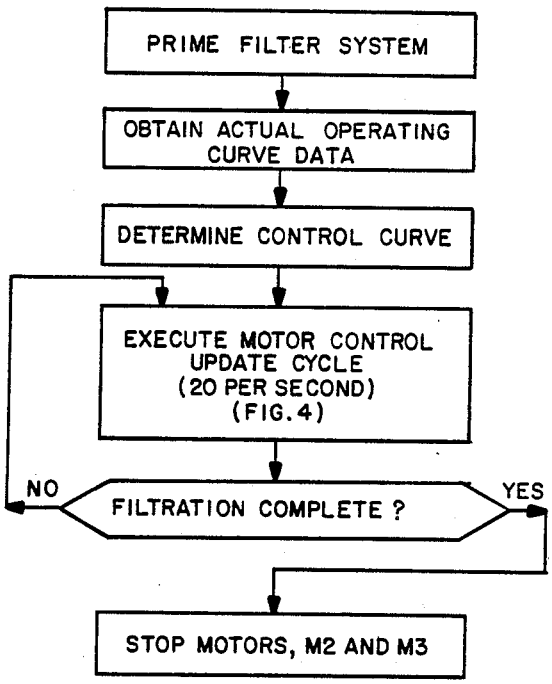
FIG. 3 is a flow chart illustrating a control sequence for the filter system shown in FIG. 1.

The operating sequence of the adaptive filter fluid flow control system 18 is illustrated in FIG. 3 to which reference is now made. As noted previously, the filter fluid flow control system 18 comprises a data processor which performs all data processing activities for the plasmapheresis system of which the adaptive filter flow control system 10 is a portion. The control system 18 controls the velocity of all motors in the plasmapheresis system including filter motor 44, motor M2 for peristaltic feed pump 58, and motor M3 for peristaltic concentrate pump 60. Normal processor operations are interrupted every 50 milliseconds to update motor velocity commands. During a typical motor control update cycle the processor detects and stores all of the feedback data, including positional and time information from the motors 44, 58 and 60 and pressure information over line 86 from P2 pressure sensor 16. The processor then updates the velocity commands for the filter motor 44, motor M2 for peristaltic feed pump 58 and then motor M3 for peristaltic concentrate pump 60.

While in general the peristaltic feed pump 58 could be utilized to control the rate of concentrate flow from filter system 12, in the present application it is desired to control the peristaltic feed pump 58 in response to an availability of feed fluid and adapt the pumping rate of peristaltic concentrate pump 60 to changes in the feed fluid flow rate to maintain a desired concentrate flow rate. Other implementations of the concepts of this invention involve the use of a filtrate pump wherein the filtrate is commanded. In the present example, optimal control is thus obtained by first updating the M2 motor velocity command for peristaltic feed pump 58 so that current velocity information is available during the course of the same update cycle when motor velocity commands for motor M3 driving peristaltic concentrate pump 60 are updated.

Operation for a given filtration operation or session begins with priming of the filter system 12 and the conduit tubing connecting the filter system 12 to the pumps 58, 60 and to filtrate container 22. This priming operation is conducted at relatively low, constant flow rates which are experimentally predetermined to be well within the flow capabilities of the system. For example, the peristaltic feed pump 58 may be operated at a flow rate of 50 milliliters per minute while the peristaltic concentrate pump 60 is operated at a flow rate of 30 milliliters per minute which accordingly results in a concentrate flow rate of 20 milliliters per minute (40% of the feed fluid flow rate) through filter system 12 and into container 22. The priming operation stabilizes system operating conditions and particularly the pressure head which becomes a constant and contributes to the 0 flow rate axis intercept of the linear prediction curve 100 (FIG. 2).

After priming has stabilized system operating points, the next executed step is to obtain actual operating curve data. During this operating step actual operating point data is sensed such as the pressure point Q, or two pressure points P and Q for filtrate flow rates of 5 add 20 milliliters per minute respectively as shown in FIG. 2. Typical sensed pressure might be 94 mm Hg at 5 milliliters per minute and 100 mm Hg at 20 milliliters per minute. When the prediction curve 100 is linearly extrapolated from these two points the linear prediction curve 100 has a slope of (Pressure Q-Pressure P) mm Hg/(20-5) ml/minute. In some cases this slope may be substantially consistent from donation to donation. In this case only a single point, such as point P or Q may be required, using a predetermined slope of 8 mm/20 ml/min for example.

In practice it has been found advantageous to use as a sensed actual operating point the average of a plurality of different data samples. The averaging of a plurality of samples tends to smooth out the substantial pressure pulses which are induced by the peristaltic feed pump, 58 and to compensate for a relatively low resolution of the P2 pressure sensor 16. While higher quality pressure sensors and data converters are of course available, for the present application it has been found that the best pressure sensor and data converter which, is economically suitable has a resolution of only 4 mm Hg in the least significant bit. By using as the final pressure value at a given operating point, an average of 4 or 5 or more samples, the effective resolution of the P2 pressure sensor 16 can be increased to about 1.5 mm Hg.

After actual operating point data has been obtained at 1 or more points such as points P and Q in FIG. 2, the control system 18 determines the control curve 104. As indicated previously, the control curve 104 may be generated by simply translating the linear prediction curve 100 upward by a fixed pressure offset value such as 12 mm Hg as in the present example. Alternative derivations may be utilized as well, depending upon the particular application.

It is desirable to use points P and Q to calculate the prediction curve 100 to accurately reflect the actual characteristics of the feed fluid, the pump flow constants, and the filter configuration. Since the curve slope and thus the extrapolated curve is generated from two relative pump command flow rates, scale errors between pump command flow rates and actual flow rates are eliminated if two or more calibration points are used.

However, in the present example it has been found to be economically expedient to use only a single actual operating point which has been selected to be point Q. Experiments have shown that for the specific application of filtering plasma from whole blood, the slope of the linear prediction curve 100 remains fairly uniform at approximately 8 mm Hg per 20 milliliters per minute flow rate from session to session notwithstanding substantial changes in the hematocrit dependent viscosity of the whole blood feed fluid. At the same time, the resolution of the P2 pressure sensor 16 is relatively coarse compared to the 8 mm Hg per 20 milliliters per minute flow rate slope of the linear prediction curve 100. As a result of these factors, it has been found advantageous for the specific application of a plasmapheresis system to use an experimentally predetermined slope of 8 mm Hg per 20 milliliter per minute flow rate for the linear prediction curve 100 and position it at the pressure point Q actually sensed at the filtrate flow rate of 20 milliliters per minute. The control curve 104 is then determined as having a 12 mm Hg offset from this linear prediction curve 100 having a predetermined slope and a vertical position (pressure offset value) determined from actual sensed operating point data.

Once the control curve 104 is established the system proceeds to execute motor control update cycles 20 times per second until the filtration process is complete. When filtration is complete the motor M3 driving concentrate pump 60 is stopped along with other motors in the plasmapheresis system.

Figure 4:
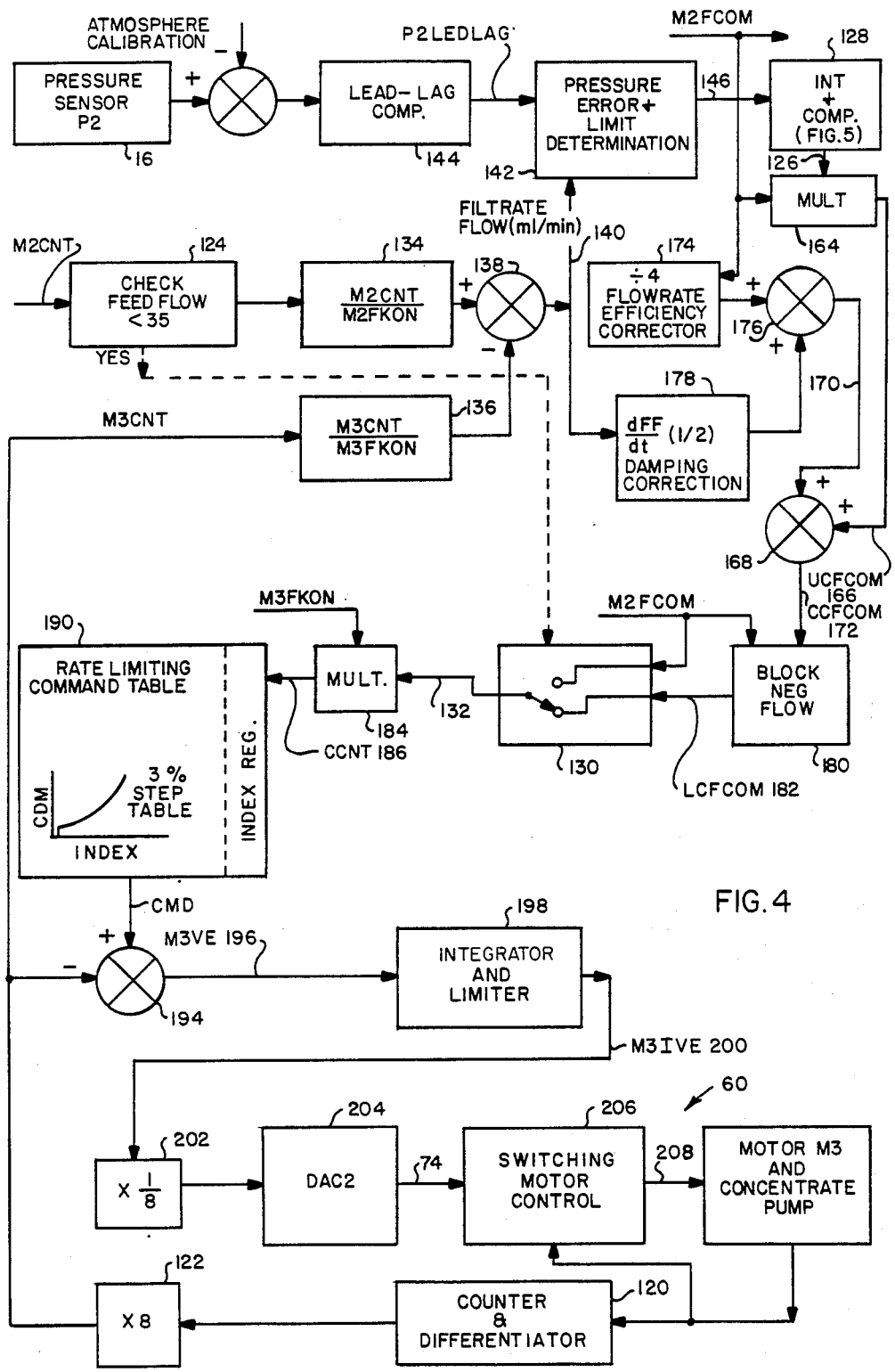
FIG. 4 is a detailed block diagram and schematic representation of a repetitive motor control update cycle shown generally in FIG. 3.

The servo control used in updating the velocity of the motor M3 driving the concentrate pump 60 is illustrated in greater detail in FIG. 4, to which reference is now made. It should be appreciated that while FIG. 4 illustrates the velocity update cycle for motor M3 in block diagram and schematic form, the mathematical and conditional operations represented by the various blocks are actually executed by the data processor comprising filter fluid flow control system 18.

As indicated previously, the velocity control update cycle begins with sensing of all system conditions and calculation of actual feedback motor velocities. The updating of motor velocity for motor M3 is typical of the procedure for all motors in the system and is executed at a counter and differentiator step 120. Employed by this step is a hardware counter which is incremented by each feedback pulse from motor M3. This counter is thus a positional reference indicating 12 times the number of revolutions of motor M3. This position count is in effect differentiated to produce a velocity signal by subtracting the position count for the previous update cycle from the present position count. The current position count is then stored for use in the next update cycle. The current velocity count is then scaled by multiplying it by eight at a step 122 to produce a motor M3 count signal M3 CNT. In similar fashion a motor 2 count signal M2 CNT is determined for the motor M2 for feed pump 58.

At step 124 the velocity signal M2 CNT is checked to see if the motor M2 has reached a velocity corresponding to a feed flow rate of 35 milliliters per minute. If yes, normal operation is assumed and a full update cycle is executed. However, if the detected feed flow velocity is less than 35 milliliters per minute, a special case (such as at startup) or other abnormal operating condition is presumed and the concentrate pump 60 is constrained to match the flow rate of the feed fluid pump 58 so that a filtrate flow rate of 0 is produced. This is accomplished by arbitrarily setting a concentrate or cell flow percent command 126 output from an integrator and comparator step 128 to a value representing 100%. As will be apparent from a more detailed description below, this corresponds to a filtrate or plasma flow rate of 0 and precludes undesirable transients in the servo loop once the feed fluid or whole blood flow rate exceeds 35 milliliters per minute and the filtrate flow rate is then permitted to ramp up from 0 to a steady state flow rate. As the integrator and comparator is set to output the 100% value a virtual switch 130 is set to produce as M3 velocity command output 132 the previously updated feed pump motor M2 flow command, M2 FCOM. This effectively commands the motor M3 to follow the velocity of motor M2.

Under normal circumstances the feed fluid flow will be 35 milliliters per minute or greater and the system then proceeds to divide signal M2 CNT by a flow constant M2 FKON at a step 134 and divide signal M3 CNT by a motor 3 flow constant M3 FKON at a step 136. These division steps 134, 136 merely provide a unit conversion from the raw motor count units to a flow rate of milliliters per minute utilized in the servo control loop. A subtractor 138 subtracts the concentrate flow rate from the feed fluid flow rate to produce a filtrate fluid flow rate signal 140 at the output thereof. This filtrate flow signal 140 becomes one input to a pressure error and limit determination step 142. Pressure error and limit determination step 142 also receives as a second input a compensated pressure signal, P2 LEDLAG, which is obtained by receiving a current actual pressure indication from P2 pressure sensor 26, calibrating the pressure signal by subtracting actual atmospheric pressure, and imposing lead lag compensation upon the calibrated pressure signal at a step 144.

Within pressure error and limit determination step 142 the filtrate flow signal 140 is utilized to access the control curve 104 (FIG. 2). The value on control curve 104 at the indicated filtrate flow rate is calculated and if this value is greater than the limit curve 110 value of 140 millimeters mm Hg, the smaller value of 140 mm Hg will be used for the control curve 104 pressure value. Normally, the actual control curve 104 pressure value will be the smaller and the compensated actual pressure value represented by signal P2 LEDLAG is subtracted from this value to produce a pressure error signal 146. The pressure error signal 146 is integrated and compensated at a step 128 which is shown in greater detail in FIG. 5 to which reference is now made.

Figure 5:
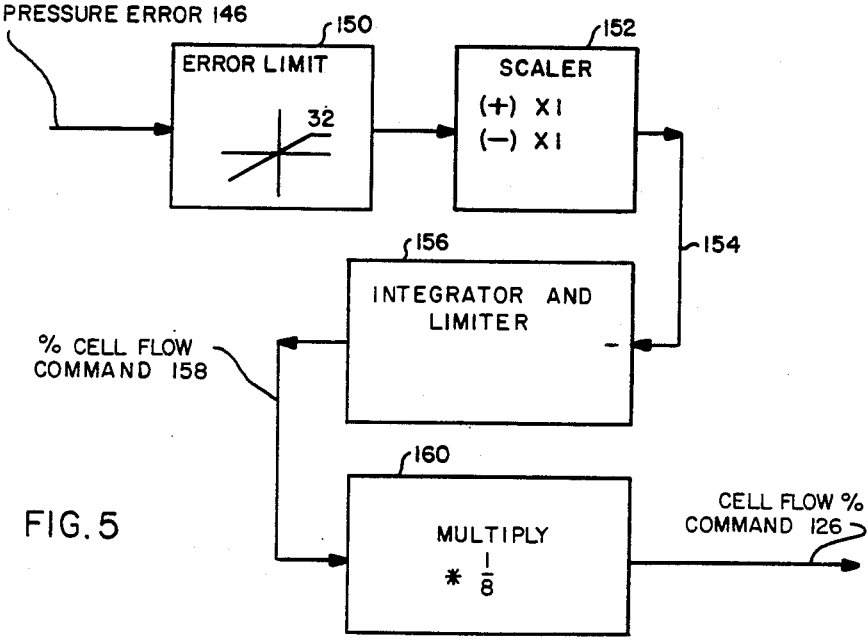
FIG. 5 is a detailed block diagram representation of a portion of the motor control update cycle shown in FIG. 4.

Referring now to FIG. 5, the pressure error signal 146 is subjected to an error limit step 150 at which a positive upper limit of 32 mm Hg is placed upon the pressure error signal 146. The limited pressure error signal is then subject to a scaler step 152 at which separate paths are available to multiply positive or negative pressure error signals by a constant. In the present application the constant has a value of "one" for both positive and negative values but the mechanism is made available to permit different scaling for positive and negative values where a particular application might make separate scaling desirable. The scaler 152 can conceptually be thought of as providing a change of units of measurement and outputs a signal 154 which is effectively a percent concentrate flow error signal.

Integrator and limiter 156 receives the percent cell flow error signal 154, performs a sign change, integrates the error signal to produce a percent cell flow command signal 158 and imposes upon the percent cell flow command signal 158 an upper limit equal to a constant P2 RSHLIM and lower limit equal to a constant P2 RSLLIM. In the present application the upper limit P2 RSHLIM has a value of 2047 corresponding to a packed cell or concentrate flow rate of 100 percent of the feed fluid flow or 0 percent filtrate flow rate. Similarly, the lower limit has a value of +266 which corresponds to a concentrate flow rate of approximately 37 percent of the feed fluid flow rate or a filtrate flow rate of a approximately 63 percent of the feed fluid flow rate. This lower limit on the percent cell flow command 158 in effect operates as a safety feature preventing excess filtrate flow through a filter.

Referring back to FIG. 4, the cell flow percent command 126 is communicated to a multiplier 164 which multiplies the cell flow percent command 126 times the commanded feed flow motor velocity command M2 FCOM and simultaneously performs a scaling function by dividing the product by 256. Output of multiplier 164 is thus an uncompensated concentrate flow command 166 commanding concentrate flow in units of milliliters per minute.

The uncompensated flow command 166 is communicated to an adder 168 where it is added to a compensation signal 170 to produce a compensated cell flow command, CCFCOM 172.

A filtrate flow rate efficiency corrector 174 receives the commanded motor 2 velocity signal, M2 FCOM, divides it by 4, and presents the result to an adder 176. The efficiency correction dynamically feeds forward a correction to substantially compensate any known filter efficiency variations as a function flow rate by adjusting the cell flow rate. For example, at a feed fluid flow rate of 60 ml per min a typical stabilized operating point might permit a yield of 80% of available plasma. If the available plasma is 60% of the feed flow rate, then the plasma or filtrate flow rate will be 48% of the feed fluid flow rate or 28.8 ml per minute. As the feed fluid flow rate increases to 100ml per min the operating point may stabilize with filtrate being only 70% of the available flow rate. This would reduce the stabilized filtrate flow rate to 42.0 ml per min.

However, if the control system follows a rapid change in feed fluid flow rate from 60 to 100 ml per min with a constant percentage filtrate flow rate, the instantaneous filtrate flow rate will be 48.0 ml per minute. This will produce a pressure error signal which will gradually reduce the filtrate flow rate to the stable 42.0 ml per min operating point. However, in the meantime the filter 32 may be experiencing irreversible plugging. The feed forward of the feed fluid command signal M2 FCOM through flow rate efficiency corrector 174 enables the motor control system to more quickly adjust to changes in feed fluid flow rates and thus reduce or eliminate periods during which the filter 32 experiences reversible blocking. A differentiating step 178 receives the actual measured filtrate flow signal 140 which is presented to the pressure error limit determination step 142, differentiates this signal 140 by subtracting from the current value thereof the value obtained in the previous update cycle, divides the difference by 2, and presents half the difference to adder 176. Adder 176 adds ½ the derivative of the filtrate flow rate to ¼ the feed fluid motor command signal to produce a compensation signal 170.

The compensated flow command 172 is communicated to a block negative flow step 180 where checks are made to assure that neither concentrate fluid nor filtrate fluid have a negative flow. Negative flow of concentrate fluid is blocked by limiting the compensated concentrate flow command 172 to a value greater than or equal to 0. Negative filtrate flow is prevented by limiting the compensated concentrate flow command signal 172 to values less than or equal to the feed flow motor velocity command signal, M2 FCOM. The block negative flow step 180 outputs a limited concentrate flow command signal 182 to the virtual switch step 130. It will be recalled that step 130 typically applies the limited concentrate flow command signal 182 to the multiplier 132. However, in the event that feed flow is less than a predetermined minimum of 35 milliliters per minute, virtual switch 130 substitutes the feed motor flow command M2 FCOM for the M3 velocity command signal 132 which is applied to the multiplier 184.

Multiplier 184 performs a scaling function to convert from milliliters per minute to flow velocity in terms of Hall device feedback counts per update cycle. Multiplier 184 multiplies the M3 velocity command signal by a motor flow constant M3FKON which relates the output concentrate count command signal 186 to the M3 velocity command 132.

The concentrate count command 186 is presented to an exponential rate limiting command table 190. Rate limiting command table 190 imposes a slew rate limit upon the change of fluid flow velocity produced by the peristaltic concentrate pump 60. In effect, the concentrate flow rate is permitted to increase at a rate of only 3% per update interval but may be rapidly decelerated. Although not specifically shown, the feed flow peristaltic pump 58 is similarly limited to flow acceleration rates of 3% per update time interval. Consequently, during transient acceleration conditions, the concentrate flow is maintained as a substantially constant percent of feed flow as the two pumps 58, 60 are being accelerated, both limited to 3% change per update cycle.

The rate limiting command table is implemented as a stored look up table storing the command values which form the output motor 3 commanded count signal, M3CCNT. These values are addressed by an index value stored in an index register within rate limiting command table 190 (physically within a data store age location in filter fluid flow control system 18). At an index value of 0 the stored command value is 0 to assure a commanded 0 velocity for the peristaltic concentrate pump 60. At an index value of 1 the command value, CMD, has an experimentally predetermined value selected to overcome system offsets and friction forces to provide the minimum value which will sustain rotation of motor M3 driving peristaltic concentrate pump 60. Thereafter, the command value, CMD, is increased by three percent for each unity increment in the index address value.

As a further limit upon the acceleration of the peristaltic concentrate pump 60, the value accessed by the current index is compared to the concentrate count signal 186 during each update cycle. If the concentrate count signal 186 is less than the value accessed by the current index, the command value, CMD, is set to the concentrate count signal 1CCNT 186. On the other hand, if the concentrate count signal 186 is greater than the stored table value accessed by the current index, the index value is incremented by 1. After a sufficient number of update cycles a steady state condition will be reached wherein the index value stored in the index register accesses a tabulated command value equal to or slightly greater than the concentrate count signal 186.

The actual M3 motor count signal, M3CNT, is subtracted from the velocity command signal, M3CCNT, at a subtracter step 194 to generate a motor M3 velocity error signal, M3VE 196. The velocity error signal 196 is then integrated at an integrator and limiter step 198 to produce an integrated velocity error signal, M3IVE 200. Integrator and limiter 198 imposes an upper limit representing 100 milliliters per minute upon the integrated velocity error signal, M3IVE 200.

Integrated velocity error signal 200 is then scaled by multiplication by ⅛ at a multiplier 202 and then communicated to a digital-to-analog converter 204 designated DAC2. Digital-to-analog converter 204 is an actual hardware device which is represented as being contained within the filter fluid flow control system 18 in FIG. 1. The analog output from DAC2 204 is communicated to a switching motor control system 206 over line 74. Switching motor control system 206 is represented as being part of peristaltic concentrate pump 60 in FIG. 1 and converts the analog velocity command received over line 74 to a switched energization pulse 208 which actually energizes motor M3 which in turn rotates the concentrate pump.

Referring again to FIG. 3, the motor control update cycle is periodically executed 20 times per second until a filtration subcycle has been completed. After completion of the filtration subcycle the feed fluid motor M2 and the concentrate fluid motor M3 are both commanded to stop and execution of the update cycle is terminated.

While there have been shown and described above particular arrangements of adaptive filter fluid flow control systems in accordance with the invention for the purpose of enabling a person of ordinary skill in the art to make and use the invention, it will be appreciated that the invention is not limited thereto. Accordingly, any modifications, variations, or equivalent arrangements within the scope of the attached claims should be considered to be within the scope of the invention.

What is claimed is:

1. A fluid flow control system for controlling a flow of filtrate through a filter system having a filter membrane with a predictable transmembrane pressure-filtrate flow rate relationship when the filter system is operated under nonobstructing operating conditions, the control system comprising:
   a flow regulating system coupled to control flows of feed fluid, concentrate fluid and filtrate fluid in the filter system in response to at least one control signal;
   a pressure sensor disposed to sense and generate indications of transmembrane pressure in the filter system; and
   a fluid flow control system coupled to receive an indication of transmembrane pressure from the pressure sensor and generate the at least one control signal to control the flow regulating system in response thereto maintain the transmembrane pressure at an intersection with a particular curve having a shape conforming to the predictable transmembrane pressure-filtrate flow rate relationship and a pressure offset from the received pressure indication by a predetermined positive pressure difference.

2. The fluid flow control system according to claim 1 above, wherein the predictable transmembrane pressure-filtrate flow rate relationship is a substantially linear relationship in which pressure increases with filtrate flow rate.

3. The fluid flow control system according to claim 1 above, wherein the fluid flow control system is operable to collect data defining an actual nonobstructing transmembrane pressure-filtrate flow rate operating point during each filtration cycle and to determine the particular control curve in response to the collected actual operating point data.

4. The fluid flow control system according to claim 2 above, wherein the fluid flow control system is operable to determine an actual nonobstructing transmembrane pressure-filtrate flow rate operating point during each filtration cycle and to determine the predictable transmembrane pressure-filtrate flow rate relationship as a straight line passing through the determined actual operating point with a predetermined slope.

5. The fluid flow control system according to claim 1 above, wherein the fluid flow control system is operable to determine a plurality of actual nonobstructing transmembrane pressure-filtrate flow rate operating points dependent upon actual feed fluid, fluid pumping system, and filter membrane characteristics encountered during each filtration cycle and to determine the particular control curve in response to the determined actual operating points.

6. The fluid flow control system according to claim 2 above, wherein the fluid flow control system is operable to determine a plurality of actual nonobstructing transmembrane pressure-filtrate flow rate operating points dependent upon actual feed fluid, fluid pumping system, and filter membrane characteristics encountered during each filtration cycle and determine the predictable transmembrane pressure-filtrate flow relationship as a straight line passing through the determined actual operating points.

7. The fluid flow control system according to claim 1 above, wherein the flow regulating system includes a concentrate pump coupled to pump concentrate fluid from the filter system and the at least one control signal from the fluid flow control system controls the pumping system by controlling the flow rate of the concentrate pump.

8. The fluid flow control system according to claim 1 above, wherein the flow regulating system includes a feed fluid pump operating to pump feed fluid to the filter system and a concentrate pump coupled to pump concentrate fluid from the filter system and wherein the at least one control signal from the fluid flow control system controls the pumping system by controlling the flow rate of the concentrate pump relative to the flow rate of the feed fluid pump.

9. The fluid flow control system according to claim 1 above, wherein the flow regulating system includes a feed fluid pump operating to pump feed fluid to the filter system and a filtrate pump coupled to pump filtrate fluid from the filter system and wherein the at least one control signal from the fluid flow control system controls the pumping system by controlling the flow rate of the filtrate pump relative to the flow rate of the feed fluid pump.

10. A fluid flow control system comprising:
a filter system having a filter membrane with a predictable transmembrane pressure-filtrate flow rate relationship when the filter system is operated under nonobstructing operating conditions;
a flow regulating system coupled to control flows of feed fluid, concentrate fluid and filtrate fluid in the filter system;
a pressure sensor disposed to sense and generate indications of transmembrane pressure in the filter system; and
a fluid flow control system coupled to receive an indication of transmembrane pressure and control the flow regulating system in response thereto to maintain the transmembrane pressure at an intersection with a particular control curve having a shape conforming to the predictable transmembrane pressure-filtrate flow rate relationship and a pressure offset from the indicated transmembrane pressure by a predetermined pressure difference.

11. A filter fluid flow control system comprising:
means for filtering coupled to receive and filter a feed fluid, the filtering means including a porous separator separating filtrate fluid from the feed fluid to produce concentrate fluid, the flow of filtrate fluid through the membrane having a predictable pressure curve characteristic for nonobstructing filtering conditions;
means for pumping disposed to control the flow of feed fluid, concentrate fluid and filtrate fluid in the filtering means;
means for sensing and indicating pressure differential across the separator; and
means for controlling fluid flow coupled to receive pressure indications from the pressure sensing and indicating means, the fluid flow controlling means being operable to control the pumping means to maintain the pressure across the separator and filtrate fluid flow rate at a point of intersection with a flow control curve having a shape conforming to the predictable pressure curve characteristic and a predetermined pressure offset relative to at least one nonobstructing filter condition actual system operating point.

12. The filter fluid control system according to claim 11 above, wherein the feed fluid is blood, the concentrate is packed cells, and the filtrate is plasma.

13. The filter fluid control system according to claim 11 above, wherein the porous separator is a rotating membrane and the filtrate has a centripetal flow direction through the rotating membrane.

14. A method of optimizing a flow of filtrate through a filter comprising the steps of:
determining a flow rate control curve in a flow rate versus transmembrane pressure coordinate system, the control curve having a shape conforming to a sensed nonobstructing concentrate flow rate versus transmembrane pressure characteristic and a predetermined pressure offset and rotation relative to the sensed nonobstructing concentrate flow rate transmembrane pressure characteristic; and
automatically controlling the filter operating point to produce filter operation at a point which intersects the flow rate control curve.

15. A method of optimizing a flow of filtrate through a filter comprising the steps of:
determining a flow rate control curve in a flow rate versus transmembrane pressure coordinate system, the control curve having a shape conforming to a sensed nonobstructing concentrate flow rate transmembrane pressure characteristic and a predetermined pressure offset and rotation relative to the sensed nonobstructing concentrate flow rate transmembrane pressure characteristic, the control curve being determined by detecting at least one nonobstructing actual filter operating point and using as the known nonobstructing concentrate flow rate pressure characteristic a prediction curve passing through the detected at least one nonobstructing actual filter operating point; and
automatically controlling the filter operating point to produce filter operation at a point which intersects the flow rate control curve.

16. The method according to claim 15 above, wherein the prediction curve is a straight line, on a linear coordinate system.

17. The method according the claim 15 above, wherein the detecting step detects exactly one nonobstructing actual filter operating point and the prediction curve is linear and has a predetermined slope.

18. The method according to claim 15 above, wherein the detecting step detects exactly two nonobstructing actual filter operating points and the prediction curve is linear and passes through the two detected nonobstructing actual filter operating points.

19. An adaptive flow filter system comprising:
a filter receiving a flow of feed fluid and separating the received feed fluid to produce separate flows of concentrate fluid and filtrate fluid;
a pumping system coupled to cause the feed fluid, concentrate fluid and filtrate fluid to flow at controlled flow rates;
a pressure sensor coupled to sense and indicate any pressure differential between the received feed fluid and filtrate fluid; and
a fluid flow control system coupled to receive pressure indications from the pressure sensor and control the pumping system in response thereto, the fluid flow control system being operable in a three dimensional pressure verses feed fluid flow rate verses filtrate flow rate coordinate system to determine at least one filter system actual operating point and to determine from the at least one actual operating point a control curve having a pressure offset relative to a locus of anticipated nonblocking actual operating points, the fluid control system being operable to control the pumping system in response to a pressure difference between an actual sensed pressure indicated by the pressure sensor and a pressure at a corresponding point on the control curve to tend to reduce the pressure difference, these relationships being scaled linearly with feed fluid flow rates.

20. The filter system according to claim 19 above wherein the fluid flow control system operates to integrate the pressure difference and control the pumping system in response to the integral of the pressure difference.

21. The filter system according to claim 20 above, wherein the pumping system includes a feed fluid pump pumping the feed fluid and wherein the fluid flow control system operates to command operation of the feed fluid pump at a commanded feed fluid velocity and to further control the operation of the pumping system to tend to reduce the pressure difference in response to a product of the integral of the pressure difference and the commanded feed fluid velocity.

22. The filter system according to claim 21 above, wherein the pumping system includes a flow rate efficiency correction to further maximize the safe operating filtrate flow rate.

23. A fluid flow control system according to claim 1 wherein the particular curve has a substantially equal pressure offset at each of a plurality of different filtrate flow rates from a prediction curve which passes through a pressure point indicated by the received pressure indication.

24. A fluid flow control system according to claim 1 wherein the particular curve has substantially no rotation relative to a prediction curve representing the predictable transmembrane pressure-filtrate flow rate relationship.

25. A fluid flow control system according to claim 1 wherein the particular curve is rotated relative to a prediction curve representing the predictable transmembrane pressure-filtrate flow rate relationship.

26. A fluid flow control system according to claim wherein the particular curve is rotated about a point thereon at flow rate of 20 milliliters per minute to reduce a slope thereof relative to a prediction curve representing the predictable transmembrane pressure-filtrate flow rate relationship.

27. A fluid flow control system according to claim 1 wherein the predetermined pressure difference is substantially equal at each of a plurality of different filtrate flow rates.

28. A fluid flow control system according to claim 10 wherein the particular control curve is rotated relative to a curve representing the predictable transmembrane pressure-filtrate flow rate relationship.

29. A fluid flow control system comprising:
a filter system having a filter membrane with a transmembrane pressure-filtrate flow rate relationship which conforms in shape and orientation to a predictable prediction curve when the filter system is operated under nonobstructing operating conditions;
a flow regulating system coupled to control flows of feed fluid, concentrate fluid and filtrate fluid in the filter system;
a pressure sensor disposed to sense and generate indications of transmembrane pressure in the filter system; and
a fluid flow control system coupled system coupled to receive an indication of transmembrane pressure at a given filtrate fluid flow rate and control the flow regulating system in response thereto to maintain the transmembrane pressure at an intersection with a particular control curve having a shape and orientation conforming to the shape and orientation of the prediction curve and a pressure offset from the indicated transmembrane pressure by a predetermined pressure difference at the given filtrate flow rate.

30. A fluid flow control system comprising:
a filter system having a filter membrane with a transmembrane pressure-filtrate flow rate relationship which conforms in shape and orientation to a predictable prediction curve when the filter system is operated under nonobstructing operating conditions;
a flow regulating system coupled to control flows of feed fluid, concentrate fluid and filtrate fluid in the filter system;
a pressure sensor disposed to sense and generate indications of transmembrane pressure in the filter system; and
a fluid flow control system coupled to receive an indication of transmembrane pressure at a given filtrate fluid flow rate and control the flow regulating system in response thereto maintain the transmembrane pressure at an intersection with a particular control curve having a shape conforming to the shape of the prediction curve and an orientation that is rotated about a given point relative to the orientation of the prediction curve.

31. A flow control system according to claim 30 wherein the control curve has a predetermined pressure offset relative to the prediction curve at a given filtrate flow rate.

* * * * *

UNITED STATES PATENT AND TRADEMARK OFFICE
CERTIFICATE OF CORRECTION

PATENT NO. : 4,879,040
DATED : November 7, 1989
INVENTOR(S) : Prince et al

It is certified that error appears in the above-identified patent and that said Letters Patent is hereby corrected as shown below:

Col. 8, line 34, "add" should be --and--

Col. 8, line 51, after "pump" delete ","

Col. 8, line 56, after "which" delete ","

Col. 17, line 29, after "claim" insert -- 1 --

Col. 16, line 26, "the" should be -- to --

Col. 16, lines 50 and 51, "verses" should be -- versus --

Col. 17, line 35, "1" should be -- 10 --

Col. 18, line 37, after "thereto" insert -- to --

Signed and Sealed this

Thirtieth Day of June, 1992

*Attest:*

DOUGLAS B. COMER

*Attesting Officer*    *Acting Commissioner of Patents and Trademarks*